United States Patent
Kasper et al.

(10) Patent No.: US 7,056,289 B2
(45) Date of Patent: Jun. 6, 2006

(54) METHOD AND SYSTEM FOR OUTPATIENT MONITORING

(75) Inventors: Edward K. Kasper, Lutherville, MD (US); Gary Gerstenblith, Reisterstown, MD (US); Sheldon H. Gottlieb, Baltimore, MD (US); Jeffrey A. Spaeder, Baltimore, MD (US); James G. Palmer, Ellicott City, MD (US); Philip R. Thorne, Mt. Airy, MD (US)

(73) Assignee: The Johns Hopkins University, Baltimore, MD (US)

( * ) Notice: Subject to any disclaimer, the term of this patent is extended or adjusted under 35 U.S.C. 154(b) by 343 days.

(21) Appl. No.: 10/415,805

(22) PCT Filed: Nov. 5, 2001

(86) PCT No.: PCT/US01/47411

§ 371 (c)(1),
(2), (4) Date: May 6, 2003

(87) PCT Pub. No.: WO02/054947

PCT Pub. Date: Jul. 18, 2002

(65) Prior Publication Data

US 2004/0034286 A1 Feb. 19, 2004

Related U.S. Application Data (60) Provisional application No. 60/246,031, filed on Nov. 6, 2000.

(51) Int. Cl.
*A61B 5/00* (2006.01)
(52) U.S. Cl. .......................... 600/300; 128/920; 705/2
(58) Field of Classification Search ........ 600/300–301; 128/920; 705/2–4; 340/573.1; 434/235–238, 434/262
See application file for complete search history.

(56) References Cited

U.S. PATENT DOCUMENTS

| | | | | |
|---|---|---|---|---|
| 5,357,427 A | * | 10/1994 | Langen et al. | 600/300 |
| 5,772,586 A | * | 6/1998 | Heinonen et al. | 600/300 |
| 5,902,234 A | | 5/1999 | Webb | |
| 5,935,060 A | * | 8/1999 | Iliff | 600/300 |
| 5,987,519 A | | 11/1999 | Piefer et al. | |
| 6,024,699 A | | 2/2000 | Surwit et al. | |
| 6,080,106 A | | 6/2000 | Lloyd et al. | |
| 6,101,478 A | | 8/2000 | Brown | |
| 6,366,871 B1 | | 4/2002 | Geva | |

FOREIGN PATENT DOCUMENTS

| | | |
|---|---|---|
| JP | 2000148889 | 5/2000 |
| WO | WO 98/02836 | 1/1998 |

* cited by examiner

*Primary Examiner*—Max F. Hindenburg
*Assistant Examiner*—Michael Astorino
(74) *Attorney, Agent, or Firm*—Francis A. Cooch (57) ABSTRACT

The present invention is an outpatient monitoring system which enables patients to interact with a health care provider using a standard telephone. A patient is presented with a series of condition-appropriate questions. Based upon the patient responses, additional questions are posed on a real-time dynamic basis. In addition, certain general questions from a predefined set of questions are asked of the patient in a rotating manner to ensure that there is variety with each telephone session. Further, the question sets can be recorded in the voice of the patient's clinician, or other person familiar to the patient, so that a familiar voice is heard by the patient, thereby personalizing the medical experience.

32 Claims, 7 Drawing Sheets

METHOD AND SYSTEM FOR OUTPATIENT MONITORING

CROSS-REFERENCE TO RELATED APPLICATIONS

This application is based on Provisional Patent Application No. 60/246,031, filed on Nov. 6, 2000, incorporated fully herein by reference.

COPYRIGHTED MATERIAL

A portion of the disclosure of this patent document contains material that is subject to copyright protection. The owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

1. Field of the Invention

The present invention relates to a method and system for interactive medical monitoring of patients by health care providers; for the gathering, analysis, storage, and presentation of patient data for use by health care providers; and for the providing of interaction between patients and health care providers at diverse locations.

2. Description of the Related Art

Effective treatment of many chronic and some acute illnesses requires frequent contact between the patients and clinicians. This frequent monitoring can significantly reduce the rate of complications and medical deterioration, and can improve the return to, and maintenance of, health of the patient. As a result, these patients experience fewer hospitalizations, improved level of health and a reduction in the cost of care provided to them.

Delivering close monitoring to outpatients is difficult to accomplish. Long-term hospitalization is not an option because it confines patients to a hospital. Frequent outpatient clinic visits present numerous logistical obstacles, which also makes it impractical. For this reason, there has been an effort to develop systems, which employ advances in the fields of computers and telecommunications, to monitor patients in their home. In general two types of systems have been developed: "Video-based," which allow a clinician to conduct an interview with a patient using a video telecommunication system; and "Store-and-Forward" based, in which specific questions are sent to the patient either in an audio or text format, and are then either played or displayed in the patient's house using a specialized communication device. The "Store-and-Forward" device then records the patient's response to the questions and forwards them back to a central computer.

The Video-based and Store-and-Forward based systems suffer from several key deficiencies. Video-based systems require an expensive specialized telecommunication device in the patient's home, and often require high bandwidth service (e.g., a T1connection) between the central device and the patient's home for efficient operation. The patient must be trained to use the system, which may be an obstacle since patients who are chronically ill often suffer from multiple co-morbidities, which affect their mobility and dexterity including heart failure, pulmonary disease, peripheral vascular disease and neurological deficits, and other conditions which might make training more difficult. Additionally, such a system requires installation in the patient's home. This limits the ease and speed with which the system can be set up and used. Even if installation is a minor obstacle, Video-based systems must be transported by the patient if they travel away from home. Finally, Video-based system requires real-time interaction between the patient and clinician and thus limits the clinician to interacting with one patient at a time, which reduces the number of patients that a clinician is able to manage.

Store-and-Forward systems also require an in-home telecommunications device and/or Internet access. These systems require training to use, and cannot be easily transported if the patient travels away from home. Store-and-Forward systems also use pre-set questions that do not change in response to the patient's answers. Additionally, the audio-based Store-and-Forward devices use synthesized or unfamiliar voices to present the questions to the patient, highlighting the impersonal nature of the interaction.

Given the limitations of current telemonitoring devices, it would be desirable to have a system that enables daily monitoring of patients without the need for specialized equipment in the patient's home, and which presents the appearance, to the patient, of a more personal medical interaction.

SUMMARY OF THE INVENTION

The present invention is an outpatient monitoring system and method that enables patients or their caregivers to interact with a health care provider using a standard household or personal communication device, such as a telephone or PDA. During a session, a patient is presented with a series of both general and condition-appropriate questions. Based upon the patient responses, additional questions may be posed on a real-time dynamic basis. Some questions are asked during each session, while certain questions from a predefined set of rotating questions are asked of the patient in a rotating manner to ensure that there is variety with each session. Further, the question sets can be recorded in the voice of the patient's clinician, or other person familiar to the patient, so that a familiar voice is heard by the patient, thereby personalizing the medical experience. Gathered data is analyzed, stored, and presented to the health care provider in a form that can be easily interpreted and accessed.

DESCRIPTION OF THE PREFERRED EMBODIMENT(S)

The following terms and definitions are used throughout the application:

"Session" means any communication between a user of the system and the system itself; for example, a "communication session" occurs when a patient connects with the health care provider server; "Repeating questions" are questions that are asked during each session;

"Rotating questions" are a predefined set of questions that are presented to the patient on a rotating basis;

A "rotating question set" is a subset of questions taken from the rotating questions and presented to a patient such that the same rotating question set is never presented to a patient in sequential sessions. A rotating question set can contain as few as one question from said rotating questions;

"Condition-specific" questions are questions that are related to a specific medical condition. For example, chronic heart failure patients frequently experience depression; the question "How would you describe your mood today?" could be considered a condition-specific question related to the condition of chronic heart failure.

"General" or "standard" questions are those questions that are not directly related to a specific condition. For example, a general question might be "Would you like to leave a message for your clinician?".

"Branching questions" are questions that may be asked, but only based upon a particular response to a previously-presented question. For example, if a "yes" response is received based upon the question "Are you more tired than usual?", additional "branching" questions may be asked to determine if the patient is experiencing dehydration, for which unusual fatigue is a symptom. Branching questions can, themselves, generate additional branching questions.

Figure 1:
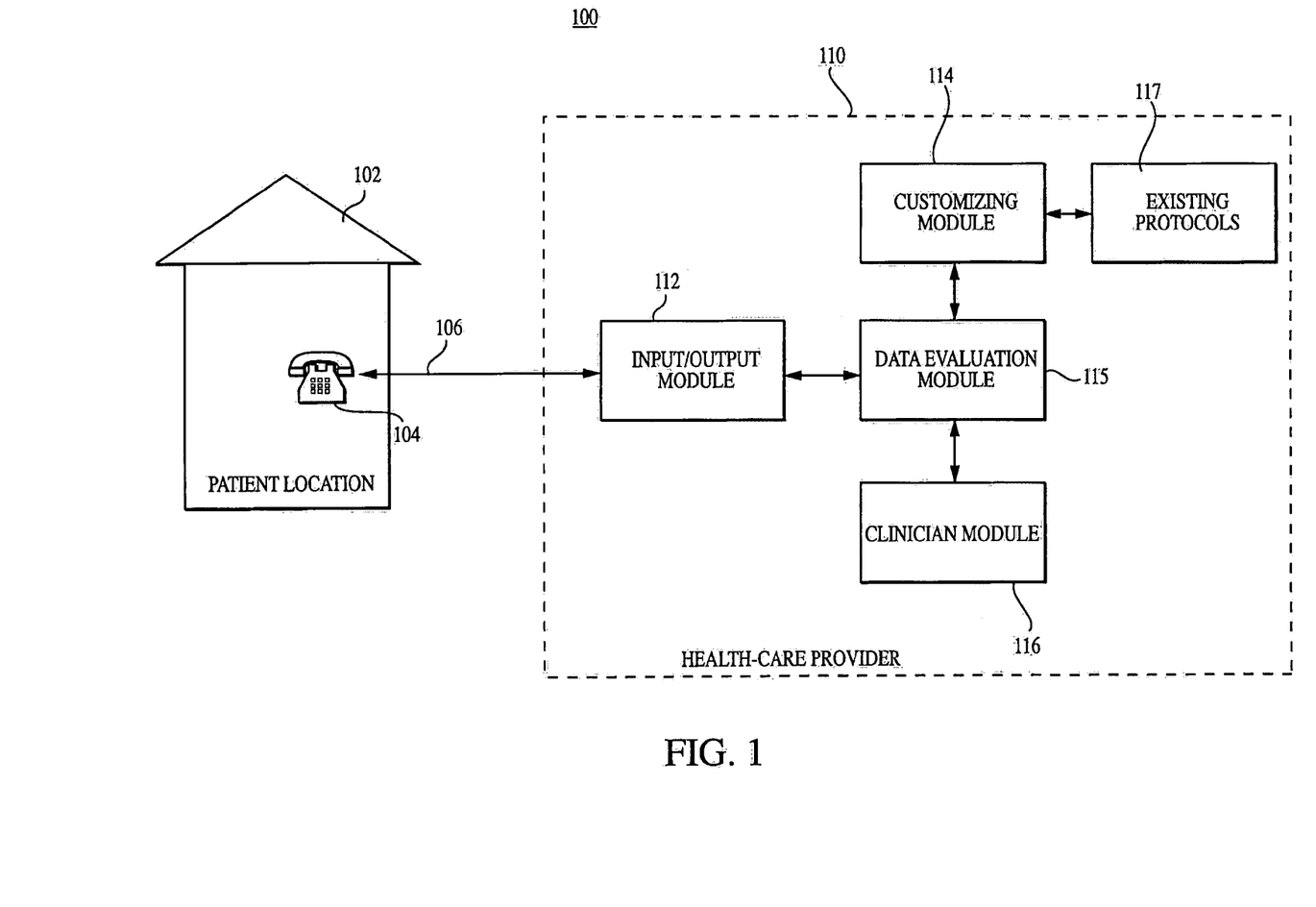
FIG. 1 is a block diagram illustrating the general overall system of the present invention.

FIG. 1 is a block diagram illustrating the general overall system of the present invention. The system 100 utilizes a communication device, such as telephone 104 situated at a patient location 102, e.g., the patient's residence, a hotel room, or any other location where the patient has access to a telephone 104. The communication device could also be an Internet-enabled computing device, such as a PDA, personal computer, etc. A health care provider facility 110 houses a server or network which includes an input/output module 112, a customizing module 114, a data evaluation module 115, a clinician module 116, and an existing protocols module 117.

In this example, the telephone 104 is connected to the health care provider location 110 via a standard telephone connection 106, e.g., a wired or wireless connection. The modules are coupled to each other either directly (e.g., by being stored on the same server) or by standard coupling means (e.g., wire or wireless connections which can comprise, for example, telephone connections, Internet connections, and the like). These different interfaces are shown generically for the different modules in FIGS. 2–6 at, respectively, 228, 340, 452, 560, and 674, Although not shown, input/output module 112 can also be configured, using conventional techniques, to provide access to the server or network housed in health care provider facility 110 via a telecommunications link such as a direct modem-to-modem connection, Internet connection, wireless connection, etc. so that authorized persons can access the system from remote locations. In a well-known manner, a patient calling in to access the system must input appropriate authentication information (e.g., user ID and password) to obtain access to the system.

Figure 2:
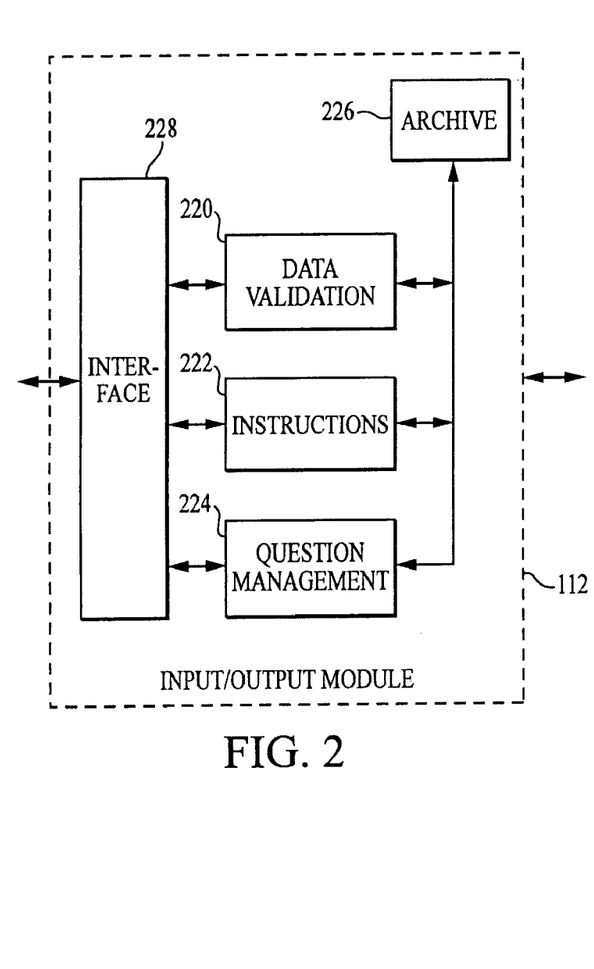
FIG. 2 is a more detailed block diagram of the input/output module 112 of FIG. 1.

FIG. 2 is a more detailed block diagram of the input/output module 112 of FIG. 1. The function of the input/output module 112 is to link the patient to the server or network at the health care provider location 110. Instructions from the clinician are stored in and conveyed to the patient using instruction module 222. The authentication information for the patient is used to match the patient with their appropriate instructions as well as to their question set(s). The question management module 224 downloads the appropriate questions from the existing protocol module 117 (or a separate database, not shown) and relays them to the patient. Question management module 224 is configured to rotate appropriate questions to the patient and also to present additional questions dependent on the patient's answers. This process is described more fully below.

Data validation module 220 compares the patient's responses to the questions with mathematical models of historical trends, thereby allowing detection of potential patient data entry errors. For example, if a response given by a patient falls outside the expected responses as indicated by the historical trend data, the patient may be notified to confirm the response, and/or the clinician may be notified to check/confirm the response. If it appears that the data is incorrect, the data validation module 220 can prompt the question management module 224 to repeat the question to the patient. This comparison is performed using conventional techniques for comparing reference or measured data/responses with historical data/responses.

Archive 226 can serve several functions, all related to information storage. Primarily, archive 226 stores a record of which questions have been asked of the patient in the past, so that the next time the patient calls, the question management module 224, after accessing archive 226 to determine which of the rotating questions were asked during the last sessions, will select different questions to be asked during the current session. This process creates the rotating question sets described above. Archive 226 can also contain a record of all clinician-patient interactions, and related data can be periodically saved in archive 226 to permit data recovery in the event of corruption or damage to the primary database.

Figure 3:
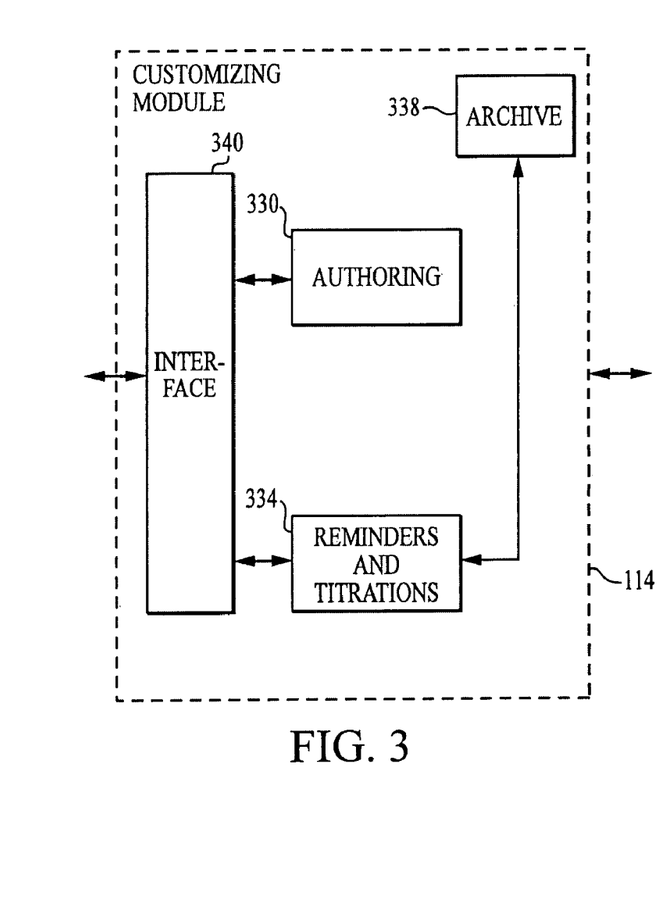
FIG. 3 illustrates a more detailed block diagram of customizing module 114.

FIG. 3 illustrates a more detailed block diagram of customizing module 114. The customizing module 114 includes authoring module 330 and reminders and titrations module 334.

Authoring module 330 allows users of the system to build the logic of new question sets that, once constructed, are recorded via voice recording module 448. This logic is a framework that is essentially a list of questions to be included in various modules, e.g., a list of questions for a diabetes module, a list of questions for a pulmonary module, etc. The logic is stored in either a repeating/rotating question set module 442 or a branching question set module 444, discussed below with respect to FIG. 4. The authoring module can be configured to present an "author" (e.g., a clinician or other medical professional) with an interface (e.g., a form with pull-down menus accessible via a PC) that allows the author to specify which questions to ask; the order in which they will be presented to the patient; which voice-recorded version of the question to use (e.g., which clinician, which language, etc.); how to group the questions; and how the questions will branch off depending upon the patient response. This logic used to select the questions is based on the medical knowledge of the author and is independent of the actual voice recording of the questions; it is simply a list of instructions directing the system how to present the questions to the patient.

Reminders and titration module 334 allows clinicians to direct the system to remind them at specific dates/times to make pre-defined changes in the dose or frequency of specific medications, depending upon the patient's condition. Further, the reminders and titration module 334 is also configured to provide the clinician customized notes or reminders on specific pre-defined dates. Like the authoring module 330, the reminders and titrations module presents the user with an interface to input general and medication-related (titration) reminders.

Archive 338 stores the reminders generated by reminders and titrations module 334, which is in turn accessed by question management module 224.

Figure 4:
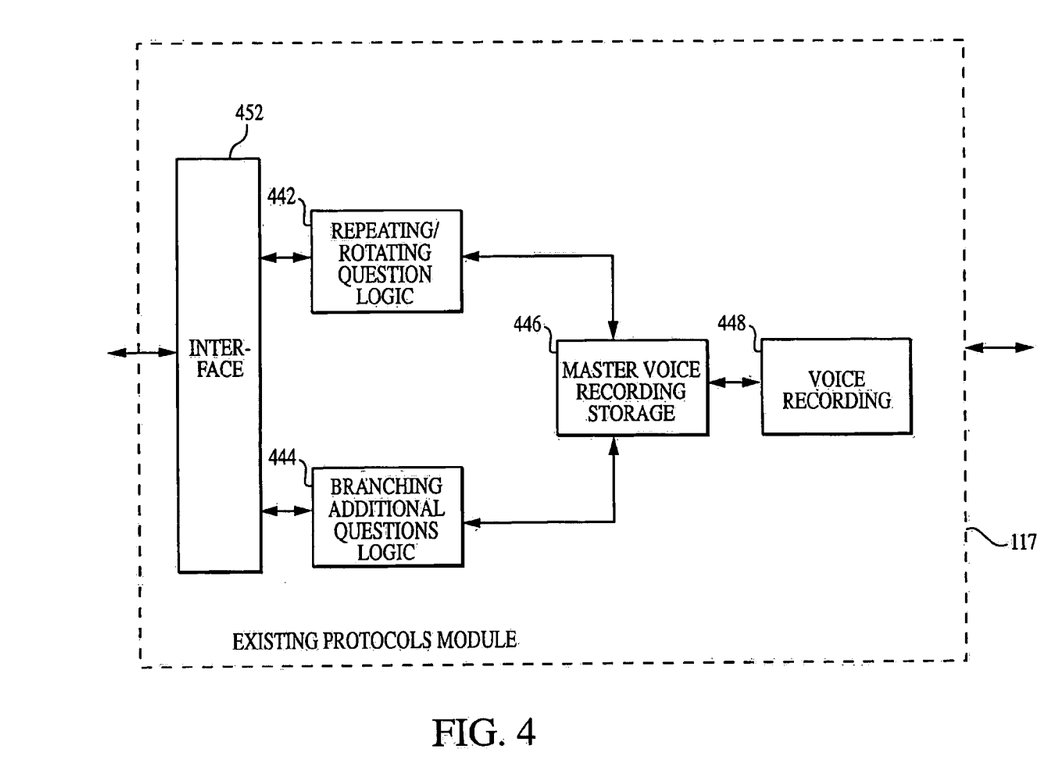
FIG. 4 illustrates a more detailed block diagram of existing protocols module 117.

FIG. 4 illustrates a more detailed block diagram of existing protocols module 117. Existing protocols module 117 contains the storage and recording elements for creation and storage of the question sets, the logic of which have been built using authoring module 330 and stored in repeating/rotating question set module 442 or branching question set module 444. Master voice storage module 446 is a master storage area where all questions, in voice format, are stored. The voice recordings are created using voice recording module 448, which can comprise any known device and/or software that enables the recording and storage of sounds in computer-readable format. As discussed above, the repeating/rotating question module 442 and branching question module 444 store the frameworks used to create the question sets presented to the patient. Each voice file stored in master voice storage module 446 corresponds to a single question in 442 and/or 444, and the same question may be recorded multiple times (e.g., by two different clinicians or in three different languages). The specific version of a question presented to the patient is determined by the logic stored in modules 442 and 444.

Figure 5:
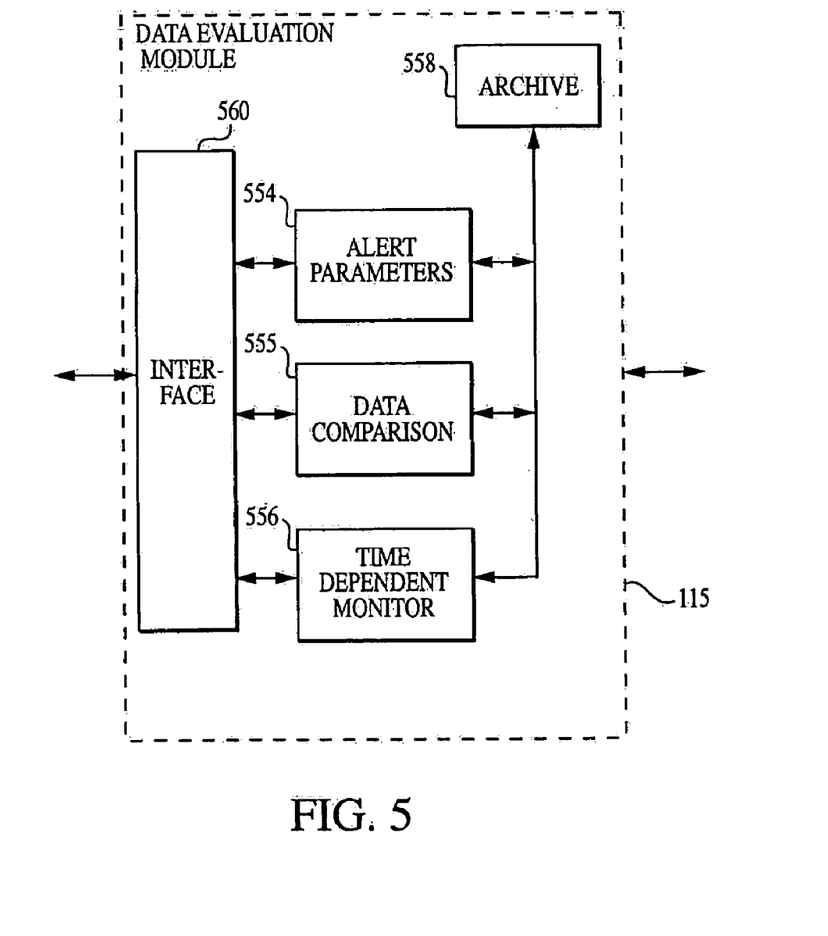
FIG. 5 illustrates a more detailed block diagram of data evaluation module 115 of FIG. 1.

FIG. 5 illustrates a more detailed block diagram of data evaluation module 115 of FIG. 1. The data evaluation module is used to evaluate the data provided by the patient via the telephone interface. An alert parameters module 554 is utilized to allow the clinician to define specific data parameters related to particular physical conditions. These alert parameters can be customized for each patient (e.g., they can be input manually to the system by a clinician accessing the system via a PC), but default settings are also available to make application of these parameters easy to enter for the clinician. These alert parameters, in conjunction with the data comparison module 555 described below, allow clinicians to be alerted as to specific symptoms such as increasing shortness of breath, chest pain, etc. These are important symptoms that would likely trigger a change in a patient's medical management.

A data comparison module 555 compares measured patient-data with the parameters specified in the alert parameters module 554. If the measured patient data as compared with these parameters indicates an abnormality, the system generates an alert indicating that a particular condition exists that requires attention.

A time-dependent monitoring module 556 is configured to alert the clinician if a patient has not called back in a defined period of time. The time-dependent monitoring function operates without a patient calling into the system; the cue for is action is the passage of time. The period of time is defined by the clinician, using the alert parameters module 554 (e.g., an alert is generated when the patient has not accessed the system for 48 hours) and/or the reminders and titrations module (e.g., an alert is generated if 3 days have elapsed since the last increase or decrease in a dosage). Therefore, if the system does not sense an expected action within a defined time period as discussed above, an alert is generated.

Figure 6:
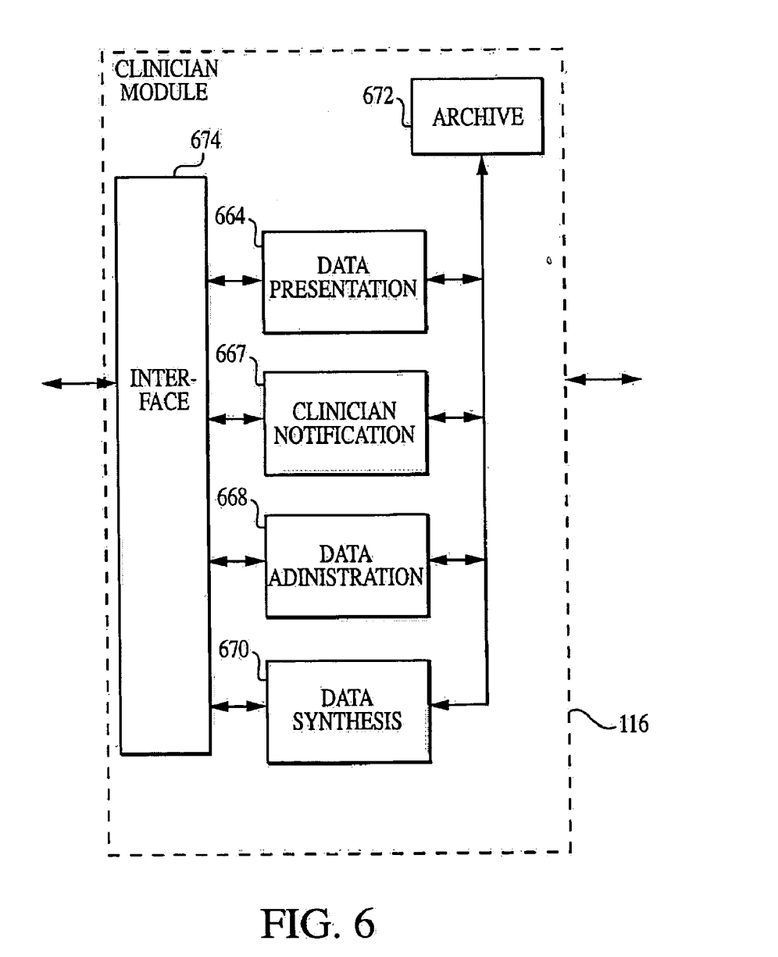
FIG. 6 illustrates a more detailed block diagram of clinician module 116.

FIG. 6 illustrates a more detailed block diagram of clinician module 116. The clinician module 116 coordinates presentation of the data, alerts, and data interpretation. Data administration module 668 stores a list of each patient and also allows the patients to be grouped into predefined groups to allow appropriate clinicians to view the data for patients for whom they are responsible. A user accessing data administration module 668 can direct the system to use a particular question set with a particular patient and have alerts and messages for that patient sent to a particular clinician or clinician group.

A data presentation module 664 presents patient-specific data into a graphical format with tables and graphs, and also makes available patient messages for review by clinicians. For example, a clinician can listen to patient messages from data presentation module 664 via a computer connection to the health-care provider location 110 if the computer is configured to play audio files, or view charts, tables, and graphs related to a particular patient.

As in the input/output module 112 of FIG. 2. archive 558 performs an information storage function for the data evaluation module 115.

Alerts generated from the data evaluation module 115 are routed to the clinician notification module 667 (which triggers a notification message to be sent to the clinician) and the data related to the alert is routed to the data presentation module 664. Once in the data presentation module 664, the data can be routed to the clinician via any known method, such as text paging, Internet, email, etc.

A data synthesis module 670 enables patient data to be summarized in a known manner for the purpose of conducting outcomes analysis, developing patient summary reviews, and generating reports that can be sent to other consulting clinicians.

Typically, the system will be monitored and administered by persons responsible for 24-hour monitoring/care of the patient, for example, nursing personnel. It should be understood the modules illustrated in FIGS. 1–6 are shown for the purposes of example only and that numerous other modules can be included depending upon the needs of the user and still fall within the scope of the present invention. For example, numerous solo-modules directed to specific illnesses may be created and accessed as needed. The modules themselves can comprise software and/or hardware configured to provide the various functional aspects described herein, using known software programming and/or hardware configuration techniques.

Figure 7:
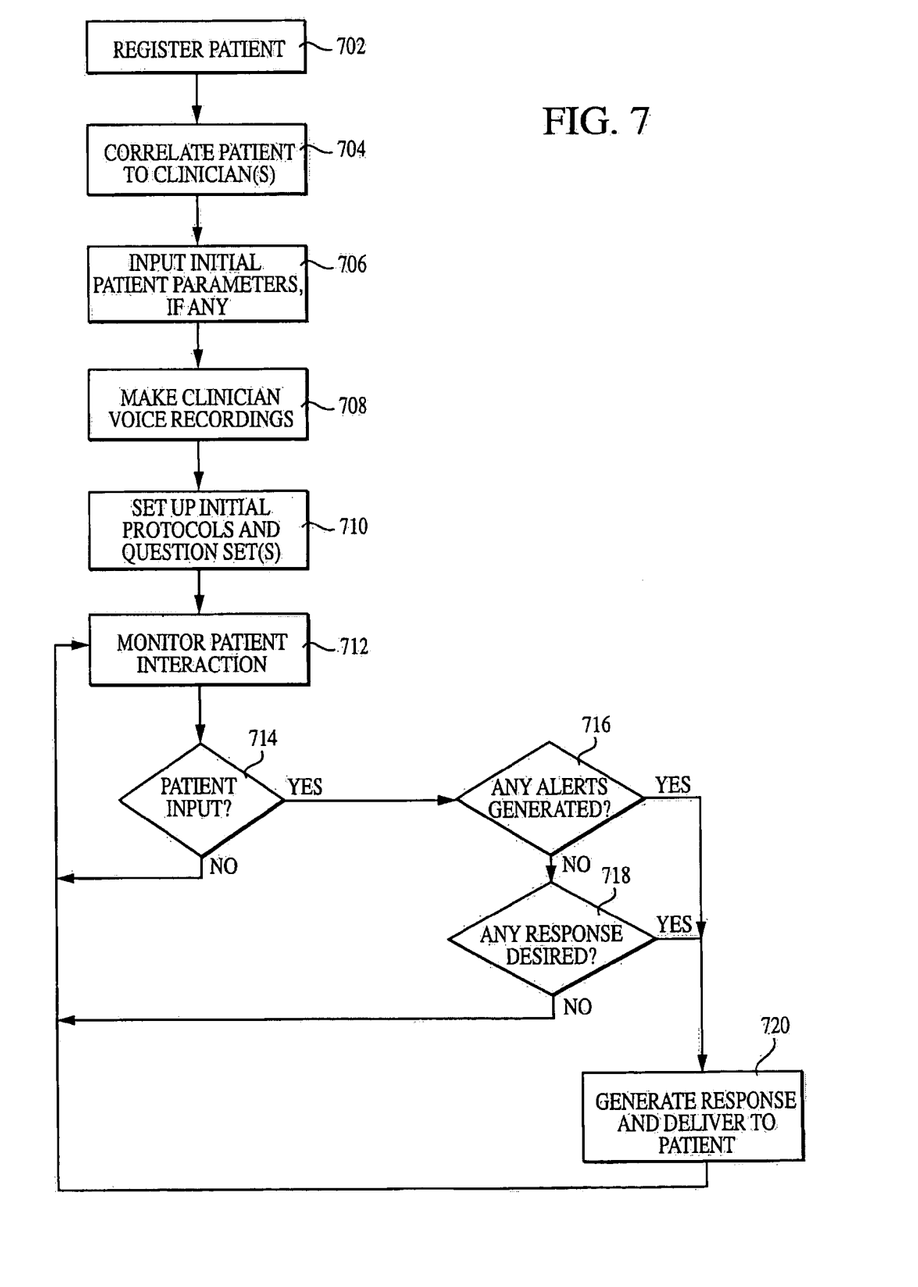
FIG. 7 is a flowchart illustrating an example of steps taken to set up the system of the present invention for operation.

FIG. 7 is a flowchart illustrating an example of steps taken to set up the system of the present invention for operation. Referring to FIG. 7, at step 702, the patient is registered in the system. This step can be performed in a variety of known manners, including by data entry at the health care provider server or by entry of the appropriate registration information by the patient via telephone 104 or by other electronic connections such as Internet connection to the health care provider servers. The registration information would include identifying information, passwords, and other basic information acquired to allow access by the patient to the health care provider's server system.

As in the inout/output module 112 of FIG. 2 archive 672 performs an information storage function for the clinician module 116.

At step 704, each registered patient is correlated to one or more clinicians so that responses and other input from the patient are routed to the appropriate clinician(s) and so that input from the various clinicians (e.g., protocol information, voice recordings, etc.) are routed to the appropriate patient.

At step 706, initial patient parameters, if any, are input to the system. This information may be physiological information, e.g., weight, height, age, etc., and/or previous medical history information and the like. As with the registration process, it is contemplated that this information may be input by the patient, the patient's caregiver, or the health care provider.

At step 708, the appropriate clinician(s) selects existing or makes additional voice recordings via voice recording module 448 and saves them on master voice storage module 446 so that the questions to be presented to the patient are available to the patient. Since the patients and clinicians have been correlated in step 704, the questions recorded will also be correlated to the appropriate patient, thereby establishing the ability for the present invention to provide questions and other information to the patient in a voice familiar to the patients.

At step 710, initial protocols and/or question sets are set up. This step involves the identification of the needs of the patient, the general questions that should be asked of the patient on a rotating basis, the condition-specific questions related to the medical protocol for the patient, the frequency of contact with the patient, alert parameters, and other related aspects of the patient's care, all of which will be automated with the inventive system.

At step 712, the patient interaction with the system is monitored. This monitoring is an ongoing process and may involve direct monitoring by 24-hour caregivers (e.g., nurses at a nursing station) and/or electronic monitoring via email, activation of text pagers, and the like directly with the clinicians.

At step 714, a determination is made as to whether or not patient input has been received. If not, the process returns to step 712, however, the system generates alerts if patient inactivity exceeds a predefined time period. If patient input is received, at step 716 a determination is made as to whether or not any alerts (described in more detail below with respect to FIG. 8) have been generated. If no alerts have been generated, the process proceeds to step 718 to determine if there is any need to respond to the patient's interaction. For example, it may be that a question asked by the patient, while not appropriate to generate an alert, might be of the type that a clinician would wish to contact the patient to discuss. These non-emergency situations, in which a response is desired or appropriate, are ascertained at step 718. If, at step 718, it is determined that no response is desired or appropriate, then the process proceeds back to step 712 to continue monitoring the patient interaction.

If at step 716 a determination is made that alerts have been generated and/or if at step 718 it is determined that a response is desired, then the process proceeds to step 720. At step 720, an appropriate response is prepared by a clinician and delivered to the patient (note that the inventive system does not perform a medical decision-making function, but rather it alerts clinicians to events or trends that may have medial significance). Such responses may be to alert emergency personnel to immediately travel to the patient location; to change medications; to initiate an office visit; to ask further questions of the patient and the like. Once the responses have been delivered to the patient, the process proceeds back to step 712 to continue monitoring patient interaction.

As can be seen, using the process described above, the patient will continually be monitored and responses from the patient will be acted upon where necessary.

Figure 8:
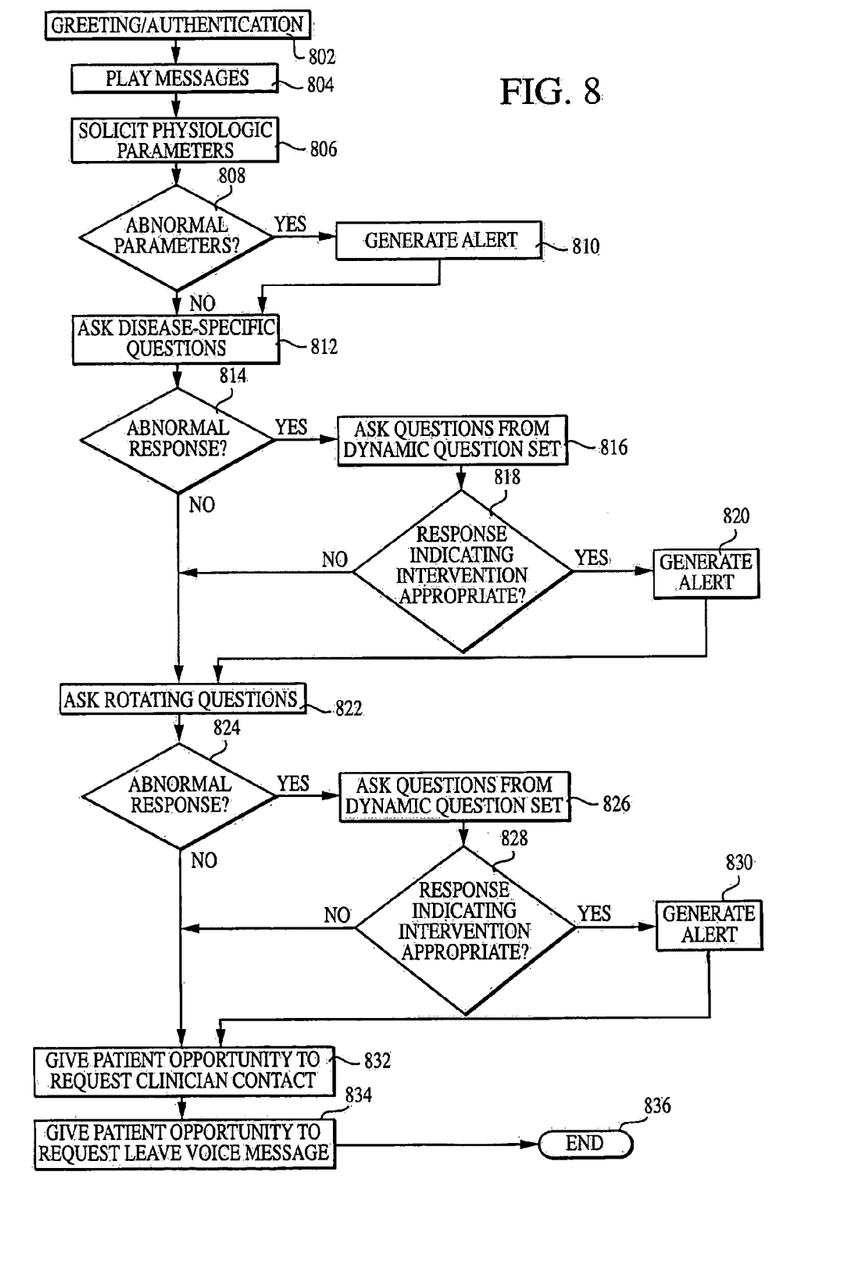
FIG. 8 is a flowchart illustrating a typical telephone session involving the present invention and the operation of the various modules described in FIGS. 1–6.

FIG. 8 is a flowchart illustrating a typical telephone session involving the present invention and the operation of the various modules described in FIGS. 1-6. In accordance with the present invention, the patient will first take measurements of the various parameters typically utilized by health care professionals to monitor patients, e.g., weight, blood pressure, pulse/ox data, respiration rate, etc. Then, the patient dials into the system using a standard telephone. At step 802, the patient receives a greeting from the system and is prompted to input information (e.g., password, etc.) that will authenticate the user.

At step 804, if any messages recorded by the caregiver are waiting for the patient, they are played at this time. At step 806, the system asks for the patient to input the physiologic parameters appropriate for their condition, however, if the patient does not have, or is unable to, provide these physiologic parameters, the system can continue to function without this information. At step 808, a determination is made as to whether or not the parameters input indicate an abnormality. If the parameters indicate an abnormality, at step 810 an alert is generated which is displayed to the health care provider, e.g., to the nurse or other staff monitoring the information incoming to and outgoing from the input/output module 112. The system then continues at step 812 where condition-specific questions, generated by existing protocols module 117, are asked. At step 814, a determination is made as to whether or not the responses to the condition-specific questions are abnormal. If not, the process proceeds to step 822. If, however, an abnormal response is received, at step 816 a questioning process based on the framework identified in the repeating/rotating question module 442 and branching additional question module 444 occurs. As described more fully below, the branching additional question set comprises a branching set of questions which, based upon the response, will generate different follow-up questions. As shown in step 818, if the responses do not indicate that an intervention is needed, then the process proceeds to step 822. If, however, the response indicates intervention is appropriate, then an alert is generated at step 820 to the supervisor monitoring input/output module 112 or to the clinicians via beeper, email, etc. The process then proceeds to block 822, where the rotating questions are asked. The rotating questions are a series of generalized questions that may or may not be asked each session, thereby reducing the very mechanical, routine nature of an automated system. The decision support module tracks which questions have been asked previously and rotates newer questions each time. This way, the patient will not receive the same set of questions each time.

Any of the questions may generate a response that triggers the questioning session to branch off into different additional questions, called "branching questions" herein. The logic for the branching questions is only activated from a patient's response to a standard question; if a question does not cause this branching-off process to occur, the branching questions will never be asked.

At block 824, if no abnormal response is received to the rotating questions, the process proceeds to step 832. If, however, an abnormal response is received, then additional questions from a dynamic branching question set, focusing on the abnormal response, are asked at block 826. If the response indicates, at block 828 that no intervention is necessary, then the process proceeds to block 832. If, however, at block 828, a response indicates that intervention would be appropriate, then an alert is generated at block 830 and the process proceeds to step 832.

At step 832, the patient is given the opportunity to request whether or not they would like a clinician to contact them, and at block 834, the patient is given the opportunity to leave a voice message for the practitioner. Finally, at block 836 the process ends. Alerts may also be activated independently of a patient response, e.g., if a patient does not call in within a preset period of time, the system will generate an alert.

Use of the present invention automates patient monitoring and yet allows it to be perceived as a more personal interaction than is available using prior art automated systems. Twenty-four hour monitoring is available with the ability to alert clinicians to immediately call back a patient where necessary; in addition, where responses can be delayed, they are provided in an automated fashion but using the voice of the clinicians with whom the patient is familiar.

Reminders can be generated to the clinicians to advise them of a need or the desirability of changing medications, dosages, etc. While these reminders can be for any aspect of the patient/clinician interaction, in the preferred embodiment these reminders fall into two main categories. The first relate to medication titrations. Many medications or treatments require a gradual increase in dose or frequency. The system allows clinicians to enter patients onto a titration schedule so that the system reminds the clinician to make a change in the dose or frequency of a treatment at predefined dates/times.

The second category, general reminders, are free text files that can be displayed on specific dates for specific patients. Examples of such free text reminders would include a reminder to call a patient who recently was started on a new therapy to ask how they were tolerating the therapy, or to contact a patient about a test that they needed to schedule.

The system is easily changeable by the health care providers at any level, e.g., nursing level, clinician level, or other support staff so that the system remains current and the patient receives the attention that is needed.

The hardware utilized to construct a system in accordance with the present invention can vary depending upon the needs and systems already in place by the user. For example, the server(s) can comprise a Microsoft Windows 2000 server having Windows 2000 PCs connected thereto for use by each medical user, e.g., cardiologist, nurse, etc. The interface between the telephone of the patient and the server provided by the health care provider can comprise, for example, an Intel Dialogic interactive voice response board, Model D/4PCI (one board per four phone lines) connected to standard commercial telephone lines. The patient telephone is simply a standard telephone connected to standard telephone lines. Measurement devices can be automatic or manual blood pressure cuffs, scales, glucometers, and the like. Standard voicemail systems can be used to facilitate the leaving of messages for patients/clinicians.

The software used to implement the various modules can be any known software platform, e.g., Visual Basic 6.0 Professional Edition.

Following are examples of question sets that can be used in connection with the present invention. They are given for the purpose of example only and it is understood that the development of numerous other question sets is contemplated and expected and that such additional question sets fall within the scope of the present invention. Further, reference is made in the following examples to various modules (e.g., the "Excess Body Fluid Module") that are not referred to in the above description of the invention; this is consistent with the statements above concerning the understanding that the various modules described above are given for the purpose of example only and that numerous other modules are contemplated that fall within the scope of the present invention. Finally, text in bold (other than headings) indicates an instruction to be carried out by the system, dependent upon patient responses (a branching question); carrying out of these instructions is what enables the present invention to pose additional questions on a real time basis that depend upon the patient's response to a prior question.

Heart Failure Disease Question Module

Physiologic Measurements
Enter your weight. Then press the # symbol.
Enter your pulse. Then press the # symbol.
Enter your systolic blood pressure, which is the larger number on your blood pressure reading. Then press the pound symbol.
Enter your diastolic blood pressure, which is the smaller number on your blood pressure reading. Then press the pound symbol.
CHF Specific Symptoms
Compared to last week are you more short of breath?—If yes activate Excess Body Fluid Module
Compared to last week is a new cough or nighttime shortness of breath interrupting your sleep or forcing you to sleep in a more upright position?—If yes activate Excess Body Fluid Module
Compared to yesterday do you have more ankle, leg or belly swelling?—If yes then activate Excess Body Fluid Module
Are you more lightheaded than usual—If yes activate Dehydration module
Have you noticed your heart racing, skipping or slowing more than usual—If yes then activate Arrhythmia Module
Did you exercise in the past day? If yes, activate Exercise Module
Ask One Question from the Standard (General) Rotating Question List
Ask One Question from the Heart Failure Rotating Question List
Patient Feedback
Did you have any difficulty using your BP cuff, scale or for any reason did you dislike using phone system today? If yes then activate HomeLink Feedback Module.
Do you want the nurse to call you? Press 1 for yes, press 2 for no
If 1, then activate nurse voicemail.
Press 1 if you would like to leave a message for the nurse, or Press 2 to end your session and record your answers.
If 1, then activate nurse voicemail.
The following questions are asked on a rotating basis of patients as they call into the system.
Standard (General) Rotating Questions
Are you having any problems getting your prescriptions refilled, paying for your prescriptions, picking up or in any other way receiving your medications?—If yes activate Medicine Availability Module.
On a scale of 1–8 how stressful is your life (1—no stress, 8—high stress)
In the past day, for any reason did you not take your medicines at the correct time or the correct dose?—If yes then activate Medicine Adherence Module
In the past week are you feeling more depressed, hopeless or have a feeling of helplessness?
Did you smoke any cigarettes or cigars in the past day?—If yes then ask 25a:
How many packs did you smoke? You may respond at any time
less than ½ pack
½–1 pack
more than 1 pack Enter the total number of alcoholic drinks, beers and glasses of wine that you drank yesterday followed by the # sign.

Did you miss a Doctor or Nurse appointment in the past week? If yes then activate Appointment module Were any of your medications or prescriptions changed in the past week?

Did you have to go to the Emergency Department or be admitted to a hospital in the past week?—If yes ask: "So that we can provide you with the best possible care, please say the name of the medical facility that treated you after the tone. Then press 2." Activate voice-recording system.

Diabetes Specific Rotating Questions (For Both Insulin Requiring and Type II Diabetes)

Have you examined your feet and looked for any blisters, sores or cuts in the past day?

Do you wear socks with all of your shoes?

Do you carry a sugar packet, candy of other food high in sugar?

If yes: Have you eaten this sugary food in the past week because you thought your sugar level was too low?

Do your shoes bind you or do your feet hurt when you walk?

Heart Failure Specific Questions

Did you measure the total amount of fluid that you drank yesterday?—If yes then ask 115a: (not shown here)

Enter the number of quarts of fluid you drank last week followed by the # symbol.

Are you more tired than usual—If yes activate Dehydration Module

Are you taking any medicines, over the counter medications or natural supplements for arthritis?

If yes: activate a voice system for the name of the medication and active a "Message alert."

Appointment Module

Did you miss the appointment because you forgot the date or time of the appointment?

Did you miss the appointment because you felt so well that you did not think you needed to come to the office?

Did you miss the appointment because you could not arrange transportation to the office?

Did you miss the appointment because you had to care for a family member or friend?

Did your miss the appointment because you had to work at your job? If yes then:

Were you unable to leave your job because you could not afford the loss of salary?

Were you unable to leave your job because you could not make arrangements with your employer?

Did you miss the appointment because of a problem with your insurance coverage?

If there is another reason why you could not come to your appointment, please leave a message after the tone: If yes, activate a voicemail system Arrhythmia Module Do you feel faint or dizzy when your heart skips beats or beats fast? If yes then create an alert.

Has there been a change in your medications in the past two weeks?

Dehydration Module

Have your diuretics, or "water pills" been increased or have you been taking more of them in the past two weeks?

Have you been drinking less water or fluids in the past one-week?

Has there been a change in any of your medications in the past one-week?

Have you experienced more diarrheas or vomiting in the past week than usual?

Diabetic Diet Compliance Module

Did you eat food that is not part of your diabetes diet because you had a meal away from your home?

Did you eat food that is not part of your diabetes diet because someone offered the food to you?

Did you eat food that is not part of your diabetes diet because no other food was available for you to eat?

Did you eat food that is not part of your diabetes diet because you did not have the time or energy to prepare or buy a more nutritious meal?

Did you eat food that is not part of your diabetes diet because you craved the taste of that food?

Decreased Food Intake Module

Did you eat less food than usual because you were too busy to eat?

Did you eat less food than usual because you were unable to buy as much food as usual?

Did you eat less food than usual because you had a poor appetite?

Did you eat less food than usual because you were dieting and trying to lose weight?

Did you eat less food than usual because you felt sick or nauseated?

Excess Body Fluid Module

In the past week, have you eaten more fast food, Asian food or foods that contain salt like snack foods, soups, or frozen dinners?

Have you, for any reason, missed taking any of your medicines in the past week?

If yes then activate the Medicine Adherence Module.

Have you been drinking more fluid than usual in the past 7 days?

Have you missed any doctor's appointments in the past 2 weeks? If yes then activate Appointment module.

Exercise Module

Enter the approximate number of minutes you exercised followed by the # symbol

Did you break a sweat during the exercise?

HomeLink Feedback Module

Did you have difficulty using the scale?

Did you have difficulty using the blood pressure cuff?

Did it take too long to complete the telephone session?

Were the telephone questions too complicated or not make sense to you?

Did you get a busy signal when you called? If yes then: Using the keypad on your phone, please enter how many times you needed to call before being connected?

Hypoglycemia Module

In the past day did you eat less food than usual, or skip a meal?

If yes, goto Decreased Food Intake Module

Did you take your diabetes medicines at the scheduled time, but eat a time that is different than usual?

Did you take more diabetes medicine than usual?

Medicine Adherence Module

Did you run out of your medications? If yes, activate Medicine Availability Module Did you purposely miss your medicines because you thought they were making you ill?

Are you feeling so well that you thought you did not need to take your medications?

Are you having problems remembering to take your medicines at the prescribed time?

Are you having problems remembering what dose of medications to take?

Is there another reason why you did not take your medicines. If yes, activate voice recording system.

Medicine Availability Module

Have your refills expired on your medicines?

Does Insurance cover at least part of the cost of your medicines?
If yes: Is the co-pay too much for your budget?
If no: Is the cost of your medications the main reason you are having difficulty getting your medications?
Have you missed medicines because you are unable to get to a pharmacy?
Have you missed medicines because the pharmacy does not have your medicines in stock?
Have you missed medicines because the pharmacy gave you the incorrect medication?
If there is another reason you missed taking your medicines. If yes activate voicemail
Medicine Adherence Module
Did you purposely miss your medicines because you thought they were making you ill?
Are you feeling so well that you thought you did not need to take your medications?
Are you having problems remembering to take your medicines at the prescribed time?
Are you having problems remembering what dose of medications to take?
Is there another reason why you did not take your medicines. If yes, activate voicemail.
Unscheduled Snack Module
Did you have a snack because you missed a meal or had too little to eat?
Did you eat a snack because you thought your glucose level was too low?
Did you eat a snack because the food was offered to you?
Did you have a snack because you craved the taste of the food?

As described above, the present invention encourages and facilitates frequent (e.g., daily) submission of measured physiological parameters by the patient to the health care provider in an outpatient setting. One benefit of the frequent submission of this patient data is that, using the ability of the present invention to convert this data into graphical format, many statistical analysis methods become available to the health care provider. For example, cumulative summation (CuSum) analysis is a known statistical technique by which variances from an established baseline are tracked, plotted and analyzed. Thus, if a patient were to only provide blood pressure information on a weekly or monthly basis, the health care professional would have no way of knowing what the blood pressure values were on the days between the two measurements. This information, however, may be very important to identifying potential problems with the patient. By receiving daily medical data and plotting it in a CuSum graph, the medical professional can identify the occurrence of significant oscillation of the measurements over a period of time and possibly identify a trend that indicates the onset of a deteriorative condition of the patient. CuSum graphing is well known; with the present invention, use of CuSum in connection with outpatient monitoring is simplified and made more accurate.

The foregoing is considered as illustrative only of the principles of the invention. Further, since numerous modifications and changes will readily occur to those skilled in the art, it is not desired to limit the invention to the exact construction and applications shown and described. Accordingly, all suitable modifications and equivalents may be resorted to, falling within the scope of the invention and the appended claims and their equivalents.

This invention claimed is:

1. A system for coordinating communication sessions between a patient location and a health care provider location to allow monitoring of a patient at said patient location by a care giver associated with said health care provider location, comprising:
   a communication device in said patient location; and
   a health care provider server located at said health care provider location, wherein:
      a patient using said system provides input data to said health care provider server using said communication device;
      said health care provider server stores data inout by said patient and presents questions to said patient; and
      if appropriate, additional questions are presented to said patient by said health care provider server based upon patient responses.
      wherein said questions presented to said patient include:
         a first question set presenting a set of repeating questions to said patient during each communication session;
         a second question set presenting a set of rotating questions to said patient during each communication session, wherein identical rotating question sets are never presented during sequential communication sessions; and
         a third question set presenting a branching question to said patient during a communication session, when warranted, based on a response from said patient to a presented question.

2. A system as set forth in claim 1, wherein said communication device is a telephone.

3. A system as set forth in claim 1, wherein said communication device is an internet-enabled computing device.

4. A system as set forth in claim 1, wherein said health care provider server includes a voice recording module, wherein said care giver records said questions using said voice recording module and presents said recorded questions to said patient.

5. A system as set forth in claim 1, wherein said health care provider server is configured to analyze data input by said patient and generate alerts to said care giver upon the occurrence of predetermined alert conditions discerned from said data.

6. A system as set forth in claim 1, wherein said health care provider server is configured to convert data input by said patient to a graphical format for display to the care giver.

7. A system as set forth in claim 6, wherein said health care provider server is configured to be remotely accessible by said care givers.

8. A system as set forth in claim 1, wherein said response from said patient to a presented question comprises a physiologic parameter.

9. A system as set forth in claim 1, wherein said communication device is wireless.

10. A method for coordinating communication sessions between a patient location and a health care provider location to allow monitoring of a patient at said patient location by a care giver associated with said health care provider location, comprising the steps of:
    providing a communication device in said patient location; and
    providing a health care provider server located at said health care provider location;
    having a patient provide input data to said health care provider server using said communication device;
    storing said patient input data on said health care provider server;

presenting one or more questions to said patient from said health care provider server, comprising at least the steps of;
  presenting a first question set of repeating questions to said patient during each communication session; and
  presenting a second question set of rotating questions to said patient during each communication session, wherein identical rotating question sets are never presented during sequential communication sessions;
  receiving patient responses to said one or more questions by said health care provider server; and
  presenting additional questions to said patient by said health care provider server based upon patient responses.

11. A method as set forth in claim 10, wherein said step of presenting additional questions to said patient comprises at least the step of;
  presenting a third question set of branching questions to said patient during a communication session, when warranted, based on a response from said patient to a presented question.

12. A method set forth in claim 11, wherein said response from said patient to a presented question comprises a physiologic parameter.

13. A method as set forth in claim 10, wherein said communication device is a telephone.

14. A method as set forth in claim 10, wherein said communication device is an internet-enabled computing device.

15. A method as set forth in claim 10, further comprising the steps of:
  making voice recordings of said questions using a voice familiar to said patient; and
  presenting said voice-recorded questions to said patient.

16. A method as set forth in claim 10, further comprising the steps of:
  analyzing said input patient data using said health care server; and
  generating alerts to said care giver upon the occurrence of predetermined alert conditions discerned from said data analysis.

17. A method as set forth in claim 10, further comprising the step of:
  converting said input patient data to a graphical format for display to the care giver.

18. A method as set forth in claim 17, wherein said graphical format is a CuSum graph.

19. A method as set forth in claim 10, wherein at least one of said patient responses comprises a physiologic parameter.

20. A method for interaction between a patient and a healthcare provider, comprising the steps of:
  providing an interactive system enabling bidirectional interactive communication between said patient and said healthcare provider;
  conveying a first query to said patient via said interactive system;
  receiving a response to said first query from said patient via said interactive system;
  conveying a second query to said patient via said interactive system, wherein said second query is selected from a set of questions, with the selection being based on said response; and
  conveying a series of rotating questions to said patient from a rotating question set, said rotating questions being of a general nature and wherein no questions from said rotating question set are repeated before every question in said rotating question set has been conveyed to said patient.

21. A method as set forth in claim 20, wherein said queries are conveyed to said patient using the recorded voice of said healthcare provider.

22. A method as set forth in claim 21, wherein said interactive system comprises a standard telephone connected to a server, said telephone being located with said patient and said server being located at a location of said healthcare provider.

23. A method as set forth in claim 20, wherein said bidirectional interactive communication is effected by the connection of said standard telephone to said server, and wherein said patient controls said interactive communication by making selection on the keypad of said telephone, and wherein said questions submitted by said healthcare provider depend upon the keypad selections made by said patient.

24. A method as set forth in claim 20, wherein said patient response comprises a physiologic parameter.

25. A system for gathering, storing, and presenting patient data, said data being transmitted to a health care provider server by a patient over a communication connection during a communication session, said system comprising:
  a repeating-question module on a computer readable medium presenting a set of repeating questions to said patient during each communication session;
  a rotating-question module on a computer readable medium presenting a set of rotating questions to said patient during each communication session, wherein identical rotating questions sets are never presented during sequential communication sessions; and
  a branching question module on a computer readable medium presenting a branching question to said patient during a communication session based on a response from said patient to a presented question.

26. A system as set forth in claim 25, wherein said communication session between said patient and said healthcare provided includes voice communication left on a voicemail system accessible by both the patient and the healthcare provider.

27. A method as set forth in claim 26, wherein said patient response comprises a physiologic parameter.

28. A system as set forth in claim 25, wherein said patient participates in said communication session using a telephone.

29. A system as set forth in claim 25, wherein said patient participates in said communication session using an internet-enabled computing device.

30. A system as set forth in claim 25, further comprising a voice recording module, wherein said healthcare provider records said questions using said voice recording module and presents said questions to said patient using said recorded questions.

31. A system as set forth in claim 25, wherein said response from said patient to a presented question comprises a physiologic parameter.

32. A system as set forth in claim 25, wherein the communication connection is wireless.

* * * * *

UNITED STATES PATENT AND TRADEMARK OFFICE
CERTIFICATE OF CORRECTION

| | | |
|---|---|---|
| PATENT NO. | : 7,056,289 B2 | Page 1 of 1 |
| APPLICATION NO. | : 10/415805 | |
| DATED | : June 6, 2006 | |
| INVENTOR(S) | : Edward K. Kasper et al. | |

It is certified that error appears in the above-identified patent and that said Letters Patent is hereby corrected as shown below:

Col. 14, Line 7, delete "inout" and substitute therefor -- input --.
Line 12, delete "." and substitute therefor --,--

Signed and Sealed this

Seventeenth Day of October, 2006

JON W. DUDAS
*Director of the United States Patent and Trademark Office*